United States Patent
Beer et al.

(10) Patent No.: US 9,658,188 B2
(45) Date of Patent: May 23, 2017

(54) ELECTROCHEMICAL TEST SENSOR

(71) Applicant: Bayer HealthCare LLC, Whippany, NJ (US)

(72) Inventors: Greg P. Beer, Cassopolis, MI (US); John P. Creaven, Pearl River, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 102 days.

(21) Appl. No.: 14/177,885

(22) Filed: Feb. 11, 2014

(65) Prior Publication Data

US 2014/0174922 A1 Jun. 26, 2014

Related U.S. Application Data

(63) Continuation of application No. 12/669,984, filed as application No. PCT/US2008/009167 on Jul. 30, 2008, now Pat. No. 8,679,309.

(60) Provisional application No. 60/962,658, filed on Jul. 31, 2007.

(51) Int. Cl.
| | |
|---|---|
| *G01N 27/327* | (2006.01) |
| *G01N 27/416* | (2006.01) |
| *C12Q 1/00* | (2006.01) |
| *G06Q 20/00* | (2012.01) |

(Continued)

(52) U.S. Cl.
CPC ......... *G01N 27/4166* (2013.01); *C12Q 1/001* (2013.01); *C12Q 1/006* (2013.01); *G01N 27/3272* (2013.01); *G06Q 20/00* (2013.01); *G06Q 20/042* (2013.01); *G06Q 20/403* (2013.01)

(58) Field of Classification Search
CPC .................. C12Q 1/001; C12Q 1/006; G01N 27/327–27/3274
USPC ....... 204/403.01–403.15; 205/775, 778, 792, 205/777.5
See application file for complete search history.

(56) References Cited

U.S. PATENT DOCUMENTS

| | | |
|---|---|---|
| 5,282,950 A | 2/1994 | Dietze et al. |
| 5,556,533 A | 9/1996 | Nozoe et al. |
| 5,762,770 A | 6/1998 | Pritchard |

(Continued)

FOREIGN PATENT DOCUMENTS

| | | |
|---|---|---|
| WO | WO 2004/051249 A1 | 6/2004 |
| WO | WO 2004/113911 A1 | 12/2004 |

OTHER PUBLICATIONS

Written Opinion corresponding to International Patent Application No. PCT/US2008/09167, dated Feb. 16, 2010, 9 pages.

(Continued)

*Primary Examiner* — Luan Van
*Assistant Examiner* — Maris R Kessel
(74) *Attorney, Agent, or Firm* — Nixon Peabody LLP

(57) ABSTRACT

An electrochemical test sensor includes a lid and a base. The base has a length and a width. The length of the base is greater than the width of the base. The base includes at least a working electrode, a counter electrode and at least three test-sensor contacts for electrically connecting to a meter. The at least three test-sensor contacts are spaced along the length of the base from each other. The base and the lid assist in forming a fluid chamber for receiving the fluid sample. The electrochemical test sensor further includes a reagent to assist in determining the concentration of the analyte in the fluid sample.

16 Claims, 9 Drawing Sheets

(51) Int. Cl.
*G06Q 20/04* (2012.01)
*G06Q 20/40* (2012.01)

(56) References Cited

U.S. PATENT DOCUMENTS

| | | |
|---|---|---|
| 2003/0203498 A1 | 10/2003 | Neel et al. |
| 2005/0098433 A1* | 5/2005 | Gundel .............. G01N 27/3272 |
| | | 204/403.02 |
| 2005/0279647 A1* | 12/2005 | Beaty ...................... B01L 3/545 |
| | | 205/792 |
| 2006/0091006 A1 | 5/2006 | Wang et al. |
| 2007/0110615 A1 | 5/2007 | Neel et al. |

OTHER PUBLICATIONS

International Search Report corresponding to International Patent Application No. PCT/US2008/09167, European Patent Office, dated Feb. 16, 2010, 9 pages.

International Preliminary Report on Patentability corresponding to International Patent Application No. PCT/US2008/09167, European Patent Office, dated Mar. 4, 2010, 10 pages.

\* cited by examiner

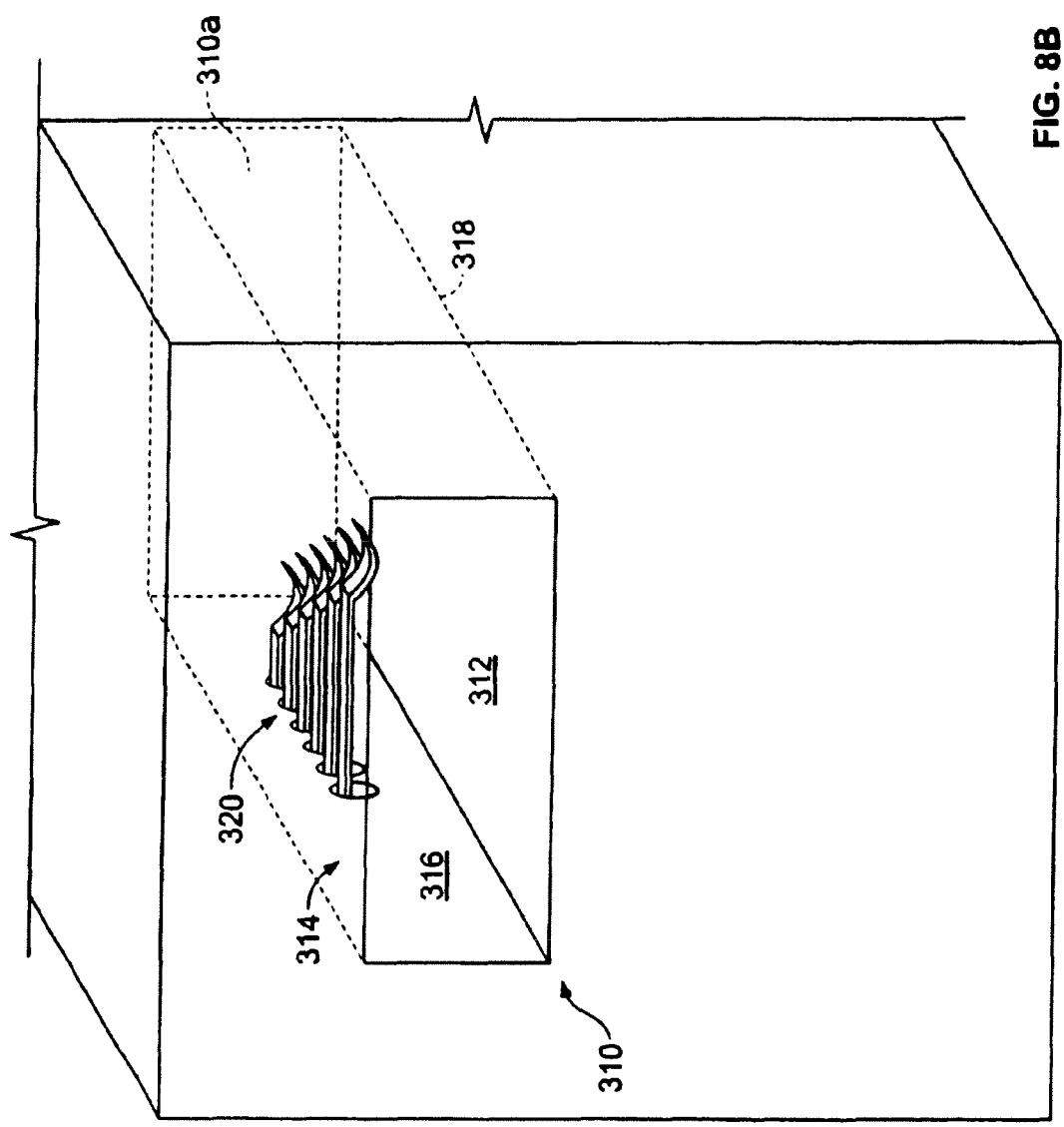

ELECTROCHEMICAL TEST SENSOR

CROSS REFERENCE TO RELATED APPLICATIONS

This application is a continuation of U.S. application Ser. No. 12/669,984 filed Jan. 21, 2010; U.S. application Ser. No. 12/669,984 filed on Jan. 21, 2010 is a nationalized application of International Application No. PCT/US2008/009167, filed Jul. 30, 2008, which is related to and claims priority to U.S. Provisional Application No. 60/962,658, filed Jul. 31, 2007, which are all incorporated by reference in their entireties.

FIELD OF THE INVENTION

The present invention generally relates to a test sensor. More specifically, the present invention generally relates to test sensors to be used with meters or instruments to determine an analyte concentration of a fluid.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, test sensors are used to test a sample of blood.

The test sensor is adapted to receive fluid (e.g., blood) from a user. The test sensor typically includes a base and a lid that is attached to the base. One type of test sensor is an electrochemical test sensor that is adapted to test for an analyte (e.g., glucose). Electrochemical test sensors typically include at least two electrodes to analyze the analyte concentration of the sample. These electrodes of the test sensor are in electrical communication with a meter or instrument that is configured to test for the analyte concentration. To improve product performance, additional electrical connections have been made between the test sensors and the meter to include functions such as auto-calibration on the test sensors or hematocrit correction. Such functions may require using additional electrodes to perform such calculations. At the same time, many at-home users strongly desire decreased size of testing materials (meter, test sensors, lancing devices, etc.). Manufacturers also desire a smaller test-sensor size so as to reduce the material costs in forming the disposable test sensors.

Therefore, it would be desirable to have a test sensor and meter that performs additional functions while still maintaining a desired size for users.

SUMMARY OF THE INVENTION

In one embodiment, an electrochemical test sensor is adapted to assist in determining the concentration of an analyte in a fluid sample. The test sensor comprises a lid and a base. The base has a length and a width. The length of the base is greater than the width of the base. The base includes at least a working electrode, a counter electrode and at least three test-sensor contacts for electrically connecting to a meter. The at least three test-sensor contacts are staggered along the width of the base from each other and are spaced along the length of the base from each other. The base and the lid assist in forming a fluid chamber for receiving the fluid sample. The electrochemical test sensor further includes a reagent to assist in determining the concentration of the analyte in the fluid sample.

In another embodiment, an electrochemical test sensor is adapted to assist in determining the concentration of an analyte in a fluid sample. The test sensor comprises a lid and a base. The base has a length and a width. The length of the base is greater than the width of the base. The base includes at least a working electrode, a counter electrode and at least three test-sensor contacts for electrically connecting to a meter. The at least three test-sensor contacts are spaced along the length of the base from each other. The base and the lid assist in forming a fluid chamber for receiving the fluid sample. The electrochemical test sensor further includes a reagent to assist in determining the concentration of the analyte in the fluid sample.

According to one method, an analyte concentration of a fluid sample is determined. An electrochemical test sensor is provided. The test sensor includes a lid, a base and a reagent that assists in determining the concentration of the analyte in the fluid sample. The base has a length and a width. The length of the base is greater than the width of the base. The base includes at least a working electrode, a counter electrode and at least three test-sensor contacts. The at least three test-sensor contacts are spaced along the length of the base from each other. The base and the lid assist in forming a fluid chamber for receiving the fluid sample. A meter is provided including a test-sensor opening. The test-sensor opening is formed between a bottom surface, a top surface and corresponding side surfaces. The side surfaces bridge the bottom and top surfaces. At least one of the side surfaces includes a plurality of side-mounted meter contacts. The test sensor is placed into the test-sensor opening such that the plurality of side-mounted meter contacts electrically contacts a respective one of the test-sensor contacts of the electrochemical test sensor. The analyte concentration is determined using electrical signals from the side-mounted meter contacts.

BRIEF DESCRIPTION OF THE DRAWINGS

FIG. 8B is an enlarged view of a test-sensor opening with side-mounted meter contacts according to one embodiment.

DETAILED DESCRIPTION OF ILLUSTRATED EMBODIMENTS

The present invention is directed to an improved electrochemical test sensor that is adapted to assist in determining the analyte concentration in a fluid. In one embodiment, an electrochemical test sensor is configured to receive a fluid sample that is analyzed using an instrument or meter. Analytes that may be measured include glucose, lipid profiles (e.g., cholesterol, triglycerides, LDL and HDL), microalbumin, hemoglobin $A_{IC}$, fructose, lactate, urea, creatinine, creatine, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids. As used within this application, the term "concentration" refers to an analyte concentration, activity (e.g., enzymes and electrolytes), titers (e.g., antibodies), or any other measure concentration used to measure the desired analyte.

In one embodiment, the electrochemical test sensor includes a base and a lid. In another embodiment, the electrochemical test sensor includes a base, a lid and a spacer. The base, lid and spacer may be made from a variety of materials such as polymeric materials. Non-limiting examples of polymeric materials that may be used to form the base, lid and spacer include polycarbonate, polyethylene terephthalate (PET), polyethylene naphthalate (PEN), polyimide and combinations thereof. It is contemplated that other materials may be used to form the base, lid and spacer.

Figure 3:
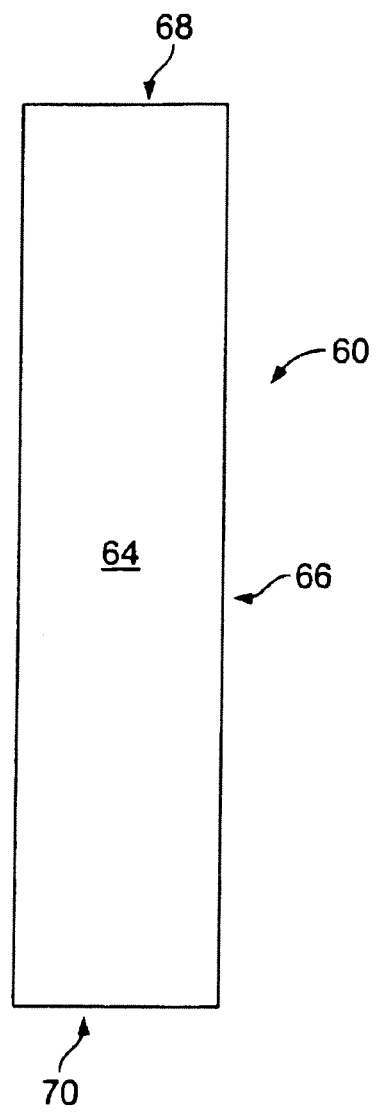
FIG. 3 is a top view of a lid to be used in forming a test sensor according to one embodiment.
Figure 4A:
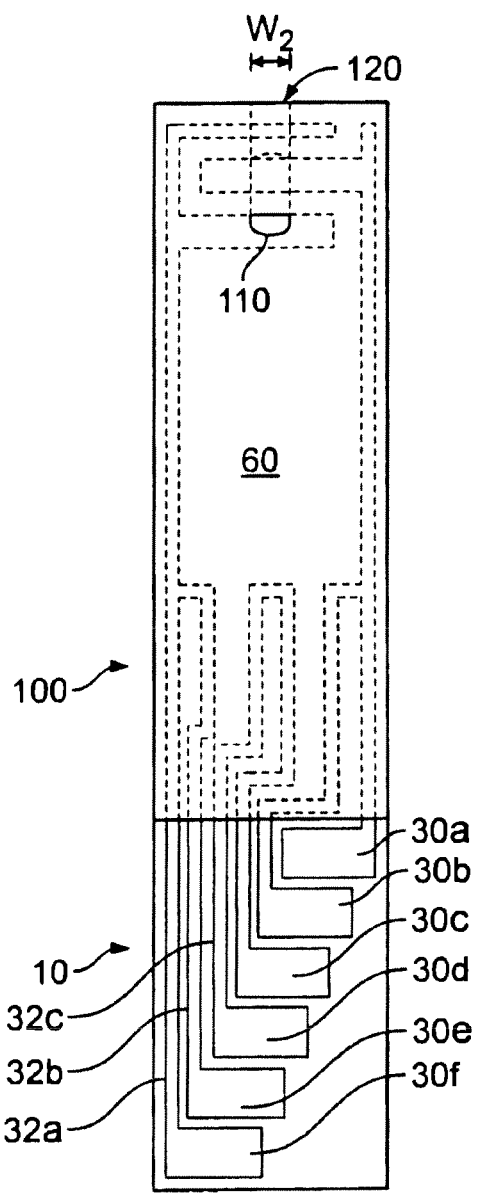
FIG. 4A is a top view of an electrochemical test sensor using the base of FIG. 1, the spacer of FIG. 2 and the lid of FIG. 3.
Figure 4B:
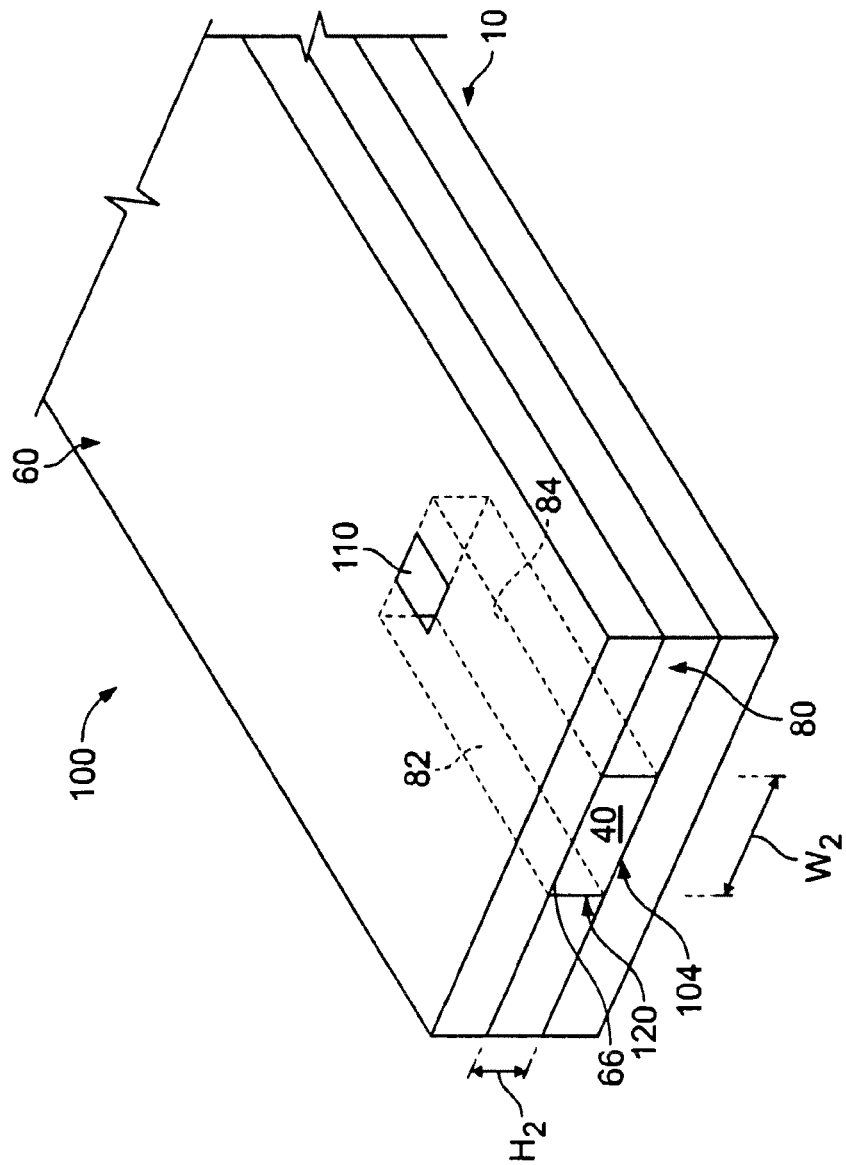
FIG. 4B is a partial front perspective view of the test sensor of FIG. 4A.

The test sensor is an electrochemical test sensor and one non-limiting example of a test sensor (test sensor 100) is shown in FIGS. 4A, 4B. The test sensor 100 of FIGS. 4A, 4B is formed using a base 10 of FIG. 1, a lid 60 of FIG. 3 and a spacer 80 of FIG. 2. When the base 10, the lid 60 and the spacer 80 are attached together, a fluid chamber 120 (see FIG. 4B) is formed. The fluid chamber 120 provides a flow path for introducing the sample into the test sensor 100 and eventually contacting the electrodes, as will be discussed below. The fluid chamber 120 also typically is in communication with at least one top vent 110. It is contemplated that in addition to, or instead of, the electrochemical test sensor may include at least one side vent.

Referring back to FIG. 1A, the base 10 includes a plurality of electrodes 22, 24, 26 and a fluid-receiving area 28 that contains an enzyme. The enzyme is selected to react with the desired analyte or analytes to be tested so as to assist in determining an analyte concentration of a fluid sample. The fluid-receiving area 28 includes a reagent 29 for converting an analyte of interest (e.g., glucose) in a fluid-test sample (e.g., blood) into a chemical species that is electrochemically measurable, in terms of the electrical current it produces, by the components of the electrode pattern. The reagent typically contains an enzyme such as, for example, glucose oxidase or glucose dehydrogenase, which reacts with the analyte and with an electron acceptor such as a ferricyanide salt to produce an electrochemically measurable species that can be detected by the electrodes. It is contemplated that other enzymes may be used to react with glucose such as glucose dehydrogenase. If the concentration of another analyte is to be determined, an appropriate enzyme is selected to react with the analyte.

The fluid-receiving area 28 may comprise a polymer, an enzyme, and an electron acceptor. The fluid-receiving area 28 may further include a mediator that is an electron acceptor and assists in generating a current that corresponds to the analyte concentration. If the enzyme is glucose oxidase, then a mediator (e.g., potassium ferricyanide) may be included. The fluid-receiving area 28 also may include additional ingredients such as a buffer and a surfactant in some embodiments.

Specifically, in this embodiment, the base 10 includes a trigger electrode 22, a working electrode 24 and a counter electrode 26. The trigger electrode 22 assists in starting the testing procedure after fluid is added to the test sensor. The flow of electrons created by the enzymatic reaction flows through the working electrode 24 to a meter or an instrument that measures the magnitude of the current flow. The counter electrode 26 provides a fixed potential against which the working electrode 24 is controlled. The potential is referenced to the oxidation/reduction potential of a respective mediator. The counter electrode may also be used to complete the electrical circuit.

The test sensor may include a detection electrode that detects an underfill condition. For example, in one embodiment, the test sensor includes a working electrode and multiple counter electrodes. In this embodiment, an analyte concentration is only reported if the tested fluid contacts both of the counter electrodes and, thus, the test sensor in this embodiment has underfill protection. In another embodiment, the plurality of electrodes includes one counter electrode and two working electrodes. In this embodiment, the analyte concentration of one working electrode should be the same or generally correspond to the other analyte concentration of the other working electrode to ensure that the sample size is sufficient. Thus, this embodiment also has underfill protection.

It is contemplated that other electrodes may be used such as a hematocrit electrode that assists in correcting for the bias that occurs with selected hematocrit concentrations. It is also contemplated that the electrodes may be used in forwarding auto-calibration information of the electrochemical test sensor to the meter or instrument.

It is contemplated that more or less electrodes may be formed in the base that is used in forming the electrochemical test sensor. For example, in other embodiments, the test sensor may include exactly two electrodes or at least four electrodes. The exactly two electrodes may be a working and counter electrode in which an electrochemically created current flows when these electrodes are electrically connected and potential created between them. It is contemplated that additional electrodes may be formed on the lid.

The electrodes may be formed on the base by a variety of methods such as, for example, printing onto the base. The electrodes are formed of conductive materials such as, for example, metallic materials (e.g., gold, platinum, palladium, rhodium, ruthenium, or combinations thereof) or carbon.

The electrodes may be defined by a laser to cut the pattern or may be defined by using a mask. For example, the plurality of electrodes 22, 24, 26 may be defined by using a mask and a laser such as, for example, an Excimer laser or a carbon dioxide-based laser. One example of a mask is a chrome-on-glass mask in which the beam of light is only allowed to pass through selected areas. According to another method, the plurality of electrodes may be defined with a laser using direct writing of the lines. In this method, the laser beam of light is moved so as to define the plurality of electrodes. Lasers that produce a beam of energy capable of removing a layer and that can be moved to form a pattern may be used in this method. Non-limiting examples of such lasers are carbon dioxide-based lasers and yttrium-based lasers such as yttrium aluminum garnet (YAG) lasers.

It is contemplated that the plurality of electrodes may be defined by other methods such as, for example, printing (e.g., screen-printing), coating (e.g., reverse roll), vapor deposition, sputtering, and electrochemical deposition.

Figures 1A, 1B:
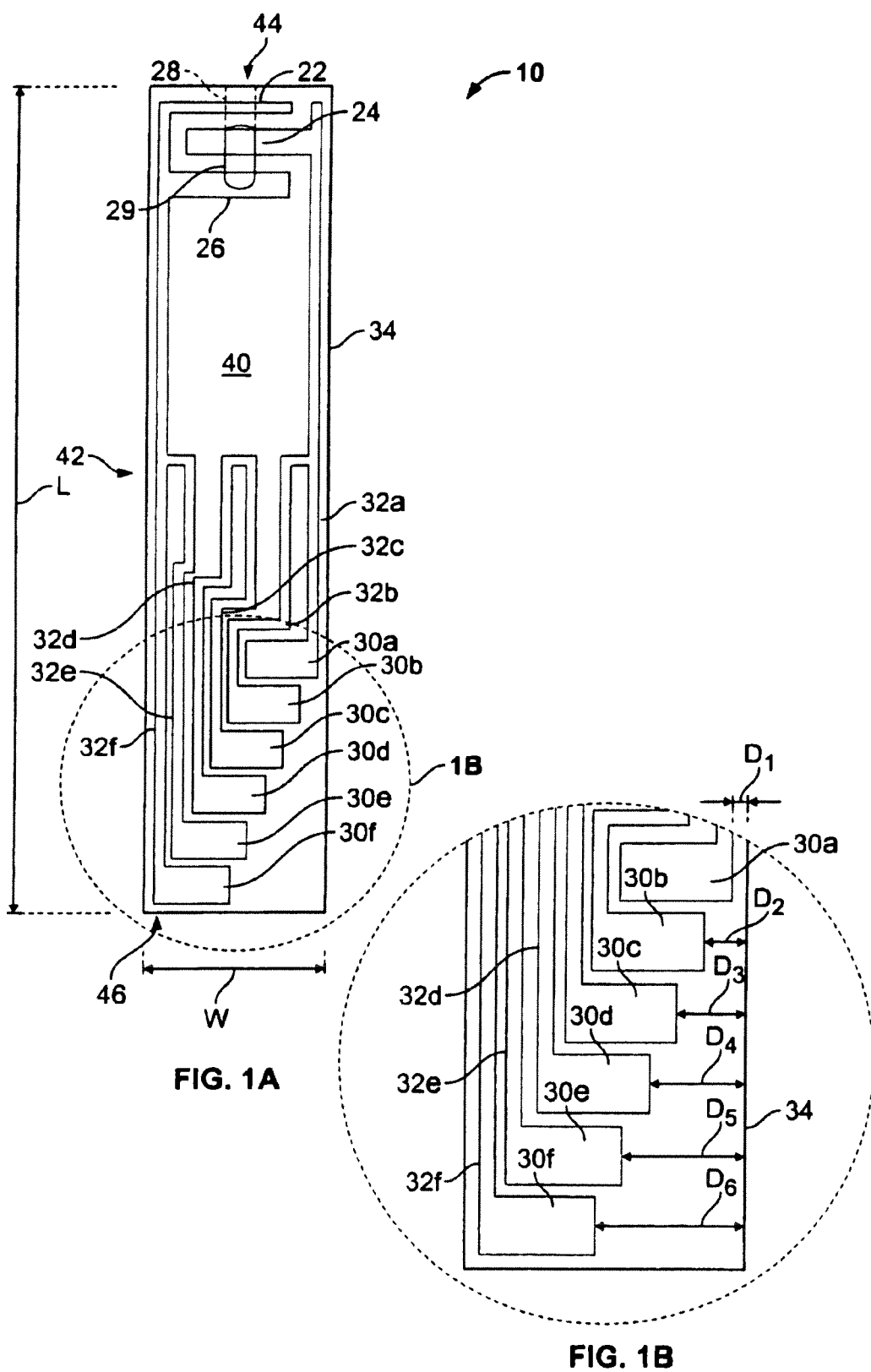
FIG. 1A is a top view of a base to be used in forming a test sensor according to one embodiment.
FIG. 1B is an enlarged view of generally circular area FIG. 1B of FIG. 1A.

The base 10 has a length L and a width W as shown in FIG. 1A. The length L of the base 10 is greater than the width W of the base 10. The length L of the base is generally at least 2 or 3 times greater than the width W of the base. Typically, the length L of the base is at least 4 or 5 times greater than the width W of the base.

The base 10 further includes a plurality of test-sensor contacts 30*a*-30*f* that electrically connects with meter contacts when the test sensor is inserted into the meter or instrument as will be discussed in more detail with respect to FIGS. 5, 6 and 8A-8C. The test-sensor contacts 30*a*-*f* are electrically connected to the electrodes via respective plurality of conductive leads 32*a*-*f*. The meter contacts typically make contact with the test-sensor contacts when the test sensor is fully inserted into the test-sensor opening of the meter or instrument. The plurality of test-sensor contacts 30*a*-*f* is shown as being polygonal shapes and, more specifically, a generally rectangular shape. It is contemplated that the polygonal shapes may be other polygonal shapes and other non-polygonal shapes. The plurality of test-sensor contacts is typically of the same shape and size, but it is contemplated that the test-sensor contacts may be of different shapes and/or sizes.

The plurality of test-sensor contacts is staggered along a width of the base in one embodiment. Specifically, in one non-limiting example, the plurality of test-sensor contacts 30*a*-*f* of FIGS. 1A, 1B is staggered along the width W of the base 10 from each other. Specifically, as shown in FIG. 1B, the test-sensor contact 30*a* is a distance D1 from an edge 34 of the base 10. The test-sensor contacts 30*b*-*f* are respective distances D2-D6 from the edge 34 of the base 10. As will be discussed below in conjunction with FIG. 5, by staggering at least some of the test-sensor contacts from each other, during insertion of the test sensor into the meter or instrument, potential scratch marks caused by the meter contacts are reduced or eliminated. It is desirable for all of the test-sensor contacts to be staggered so as to reduce or eliminate the potential scratch marks caused by the meter contacts. Specifically, the meter contacts should not desirably create scratches that prevent or inhibit good electrical contact for subsequent test-sensor contacts traveling along the surface of the test sensor. Thus, a test sensor having staggered test-sensor contacts enhances the robustness and reliability of the resultant electrical contact between the test sensor and the meter or instrument.

The base 10 of FIG. 1 includes an upper base surface 40 and a lower base surface 42. The base 10 includes a first base end 44 and a second base end 46, in which the first base end 44 and the second base end 46 are located on opposing ends of the base 10. Similarly, the lid 60 of FIG. 3 includes an upper lid surface 64 and a lower lid surface 66. The lid 60 includes a first lid end 68 and a second lid end 70, in which the first lid end 68 and the second lid end 70 are located on opposing ends of the lid 60. The lower lid surface may be treated with surfactant to enhance the sample harvesting or coated with a hydrophilic coating to enhance test-sensor filling.

Figure 2:
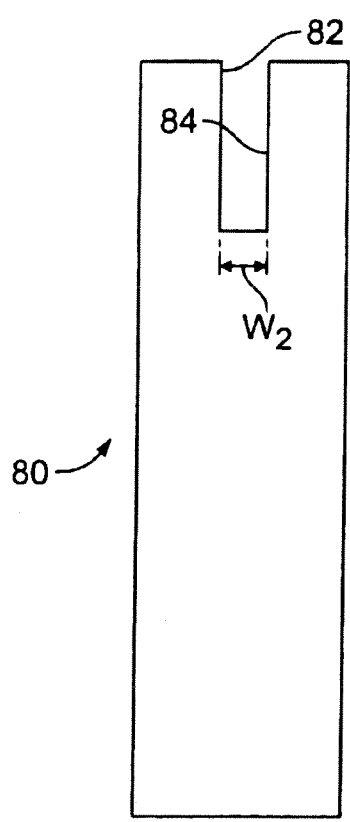
FIG. 2 is a top view of a spacer to be used in forming a test sensor according to one embodiment.

The spacer 80 of FIG. 2 includes a distance W2 being formed between a first side 82 and a second side 84. The distance W2 will form the width of the fluid chamber 120 of the test sensor 100 (FIGS. 4A, 4B). Referring back to FIG. 2, the distance W2 is shown as being generally constant between the first and second sides 82, 84. It is contemplated, however, that the distance between the first and second sides may vary. The spacer 80 is shown as being a one-piece integrally formed structure. It is contemplated in other embodiments that the spacer may be formed using a plurality of sections.

Examples of components, such as those mentioned above, used in forming electrochemical test sensors, including their operation, may be found in, for example, U.S. Pat. No. 6,531,040 B2.

To form the test sensor 100 of FIGS. 4*a*, 4*b*, the base 10, the spacer 80, and the lid 60 are attached. In one embodiment, the base 10 and the spacer 80 are attached via an adhesive and the spacer 80 and the lid 60 are attached via an adhesive. It is contemplated that other materials may be used that have sticking properties such that the lid, base and spacer remain attached.

The base 10 may be laminated to the spacer 80 using, for example, a pressure-sensitive adhesive and/or a hot melt adhesive. Thus, the lamination between the base and the spacer uses pressure, heat or the combination thereof. It is contemplated that other materials may be used to attach the base to the spacer. Similarly, the lid 60 and the spacer 80 may be attached using the same or a different adhesive than the adhesive used between the base 10 and the spacer 80.

It is contemplated that the base and spacer may be attached by other methods such as heat sealing. Similarly, the lid and the spacer may be attached by other methods such as heat sealing. Thus, in this embodiment, the test sensor includes a base, a spacer and a lid without an adhesive layer. For example, the spacer may be made of a lower melting temperature material than the lid and the base. The heat sealing may be accomplished by, for example, sonic welding.

In another embodiment, the lid or base may be heat-sealed to the spacer with the remaining one of the lid and base being adhesively attached to the spacer. For example, the lid and spacer may be heat sealed while the base is attached to the spacer via an adhesive layer.

According to another embodiment, a spacer-lid combination is used in which the spacer and lid have been previously attached before being attached to the base. According to a further embodiment, a spacer-base combination is used in which the spacer and the base have been previously attached before being attached to the lid.

After the base 10, lid 60 and spacer 80 are attached, the fluid chamber 120 is formed between a portion of the lower lid surface 66, the upper base surface 40 and the first and second sides 82, 84. The fluid chamber 120 is formed between the lower lid surface 66 and the upper base surface 34 at or near the first lid end 68 and the first base end 44 (see FIGS. 1A, 3). As shown in FIG. 4B, the fluid chamber 120 is adapted to receive a fluid from a fluid-receiving end 104.

The fluid chamber 120 as shown in FIG. 4B has a height H2 that is generally from about 1 to about 10 mils. More specifically, the fluid chamber 120 as shown in FIG. 4B, has a height H2 that is generally from about 3 to about 7 mils. Similarly, the fluid chamber 120 as shown in FIG. 4B has a width W2 that is generally from about 1 to about 120 mils. More specifically, the fluid chamber 120 as shown in FIG. 4B, has a width W2 that is more typically from about 20 to about 80 mils. It is desirable for the height H2 and width W2 to be able to receive the fluid (e.g., blood) from a user while still maintaining the blood within the confines of the fluid chamber 120. It is contemplated that the fluid chamber may be of other shapes and dimensions.

The fluid chamber is in communication with at least one vent. As shown in FIG. 4B, the fluid chamber 120 is in communication with the vent 110. The vent assists in making the fluid (e.g., blood) flow into the fluid chamber 120 of the test sensor via capillary action. In an electrochemical test sensor, the at least one vent typically is located around or just past the working/counter electrode area.

Figure 5:
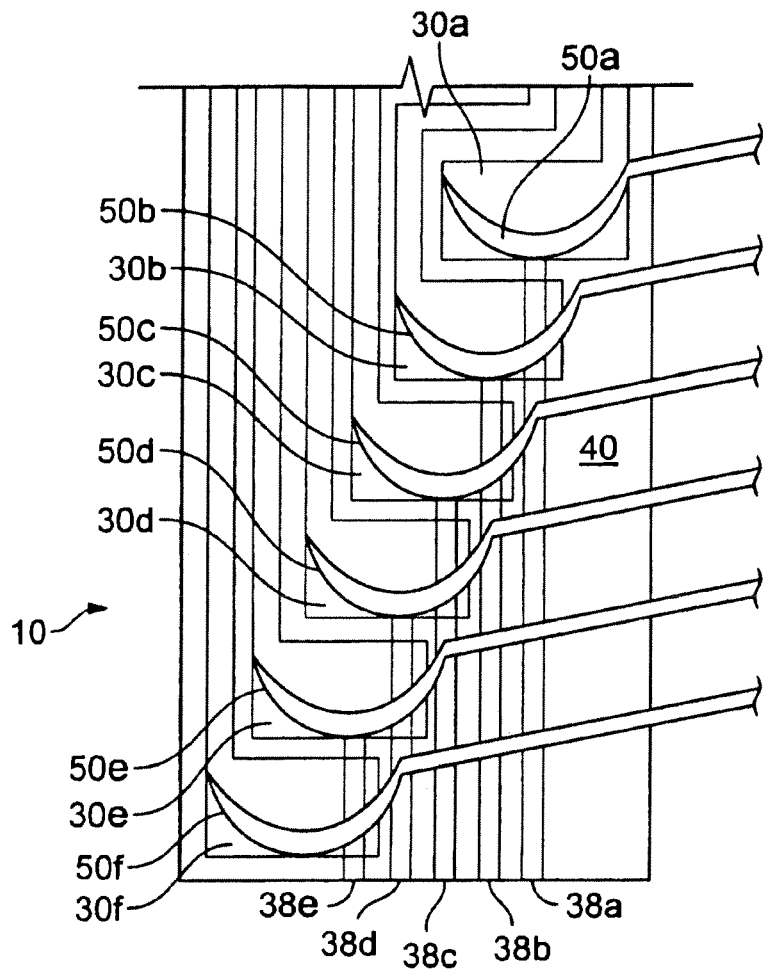
FIG. 5 is an enlarged view of FIG. 1B that depicts potential scratch marks and meter contacts according to one embodiment.
Figure 6:
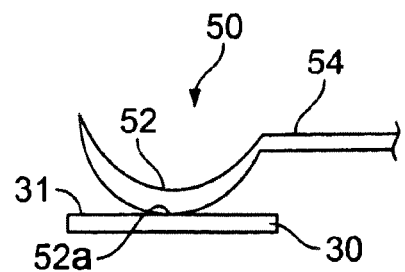
FIG. 6 is an enlarged side view of a meter contact contacting a test-sensor contact in a proper orientation according to one embodiment.

A non-limiting example of how the scratch marks can be reduced or eliminated is shown in FIG. 5. FIG. 5 is a schematic that depicts the base 10 of FIGS. 1A, 1B with the addition of a plurality of potential scratch marks 38a-38e being made from a respective plurality of meter contacts 50a-e of the meter or instrument. In the embodiment shown in FIG. 5, meter contact 50f would contact the test-sensor contact 30f without traveling much, if any, on the surface of test sensor such that a potential scratch mark has not been shown. The orientation of the plurality of meter contacts has been modified in FIG. 5 so as to better depict where the meter contacts 50a-e contact the top surface 40 of the base 10 during insertion of the test sensors into the meter or instrument. The correct orientation is depicted and described below in conjunction with FIG. 6.

Figure 7:
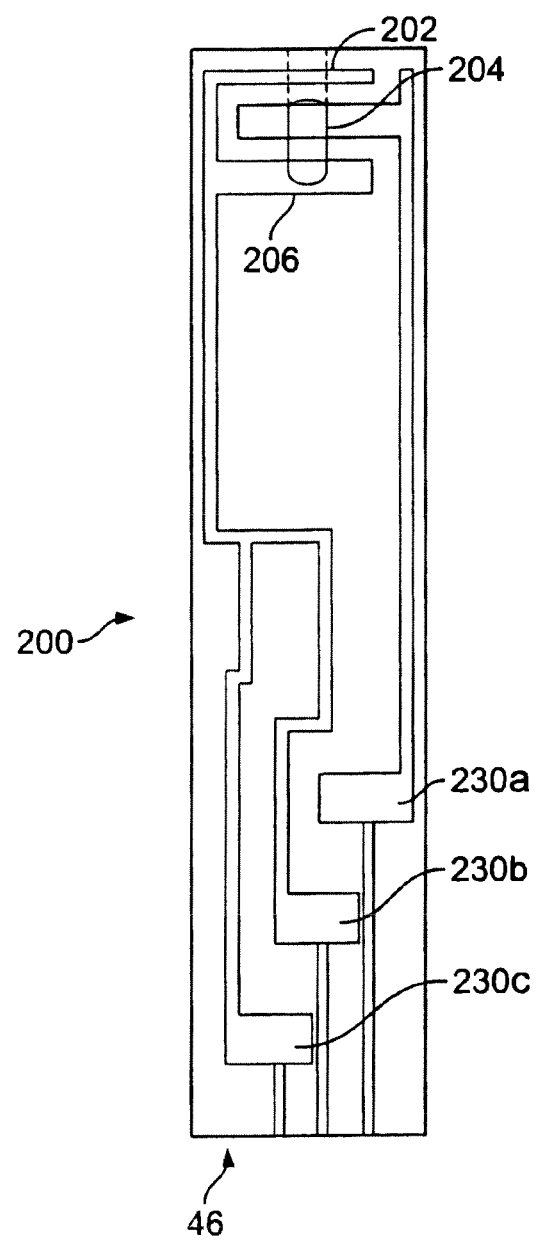
FIG. 7 is a top view of a base to be used in forming a test sensor according to another embodiment.

Referring still to FIG. 5, a potential scratch mark 38a would not contact any area of the test-sensor contacts 30c, 30d, 30e or 30f. It is contemplated that the test-sensor contacts could be of a sufficient number and sufficient size that any potential scratch marks would not interfere at all with any of the test-sensor contacts. For example, referring to FIG. 7, a test sensor 200 includes a plurality of electrodes 202, 204 and 206, and exactly three test-sensor contacts 230a-c in which any potential scratch marks would not interfere at all with any of the test-sensor contacts.

Referring back to FIG. 6, a single meter contact 50 is shown with respect to a single test-sensor contact 30. The meter contact 50 includes a contact section 52 and a side-extension section 54. The contact section 52 includes a surface 52a in which a portion of the surface 52a contacts an upper surface 31 of the test-sensor contact 30. The portion of the surface 52a contacting the upper surface 31 has the potential of leaving scratch marks as discussed above. It is desirable to have a sufficient area of the surface 52a contacting the upper surface 31 such that a good electrical connection is formed between the meter contact 50 and the test-sensor contact 30. To reduce wear and potentially reduce any scratch marks depending on the configuration of the test-sensor contacts, the area of the surface 52a contacting the upper surface is of no greater size than that needed to establish a good electrical connection between the meter contact 50 and the test-sensor contact 30.

The shape of the meter contact 50 and, more specifically, contact section 52 is of a generally crescent or spoon shaped. To further reduce the likelihood of forming scratch marks on the test sensors, the contact section 52 is desirably generally smooth. It is contemplated that the meter contact 50 may be of other shapes and sizes than depicted in FIG. 6.

Figure 8A:
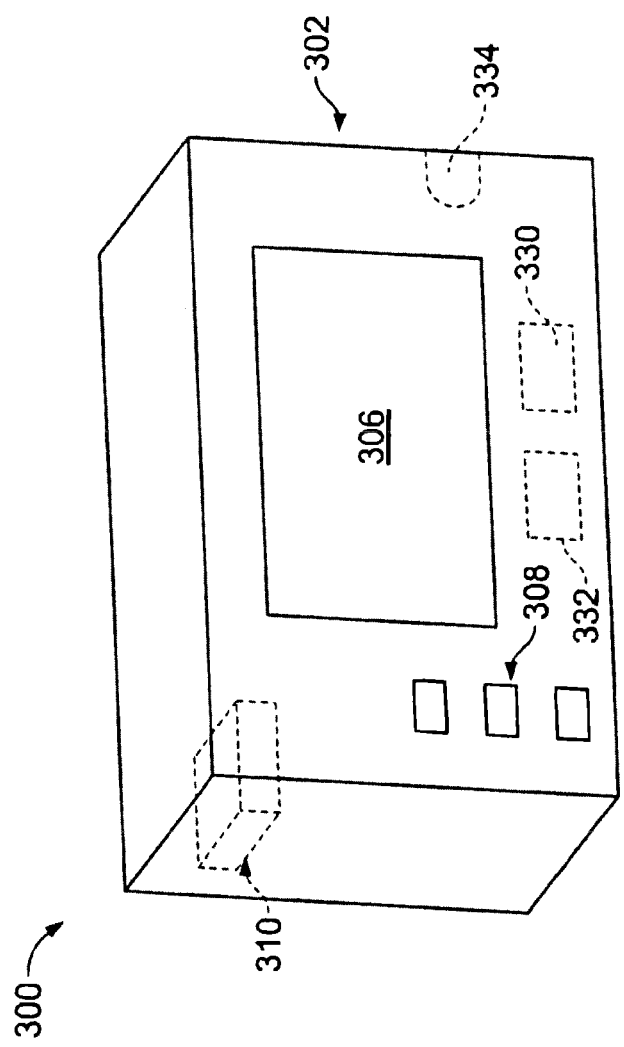
FIG. 8A is a meter or instrument with a test-sensor opening according to one embodiment.

Referring to FIG. 8A, an analyte-determining meter or instrument 300 is shown according to one embodiment. In one embodiment, the analyte-determining instrument 300 comprises a housing 302, a display 306, at least one user-input mechanism 308, a test-sensor opening 310, a memory device 330 and a processor 332. The housing 302 is adapted to assist in protecting the components of the analyte-determining instrument 300. The display 306 is adapted to display information to a user of the instrument 300. Some of the information that may be displayed to a user includes analyte-concentration readings, time and date indicators, hematocrit readings, markers, alarms and any combinations thereof. It is contemplated that other information may be displayed. The display may include different types of displays. For example, the display 306 may include an LCD display, a graphics display, a plasma display, a backlit display, a combination segmented/graphic display or any other suitable display.

The at least one user-input mechanism 308 allows the user to make selections relating to one or more user features of the instrument 300. The user-input mechanism 308 may include, for example, buttons, scroll bars, touch screens, or any combination of such items.

The test-sensor opening 310 is shown in more detail in the enlarged view of FIG. 8B. The test-sensor opening 310 has a bottom surface 312, a top surface 314 and corresponding side surfaces 316, 318. The side surfaces 316, 318 bridge the bottom and top surfaces 312, 314. At least one of the side surfaces includes a plurality of side-mounted meter contacts. Specifically, in FIG. 8B, the side surface 316 includes a plurality of side-mounted meter contacts 320 that contacts the test-sensor contacts after the test sensor has been inserted into the meter or instrument 300. By mounting the meter contacts from a side wall, significantly more meter contacts can be employed without increasing the width of the test sensor or overall size of the test sensor.

Figure 8C:
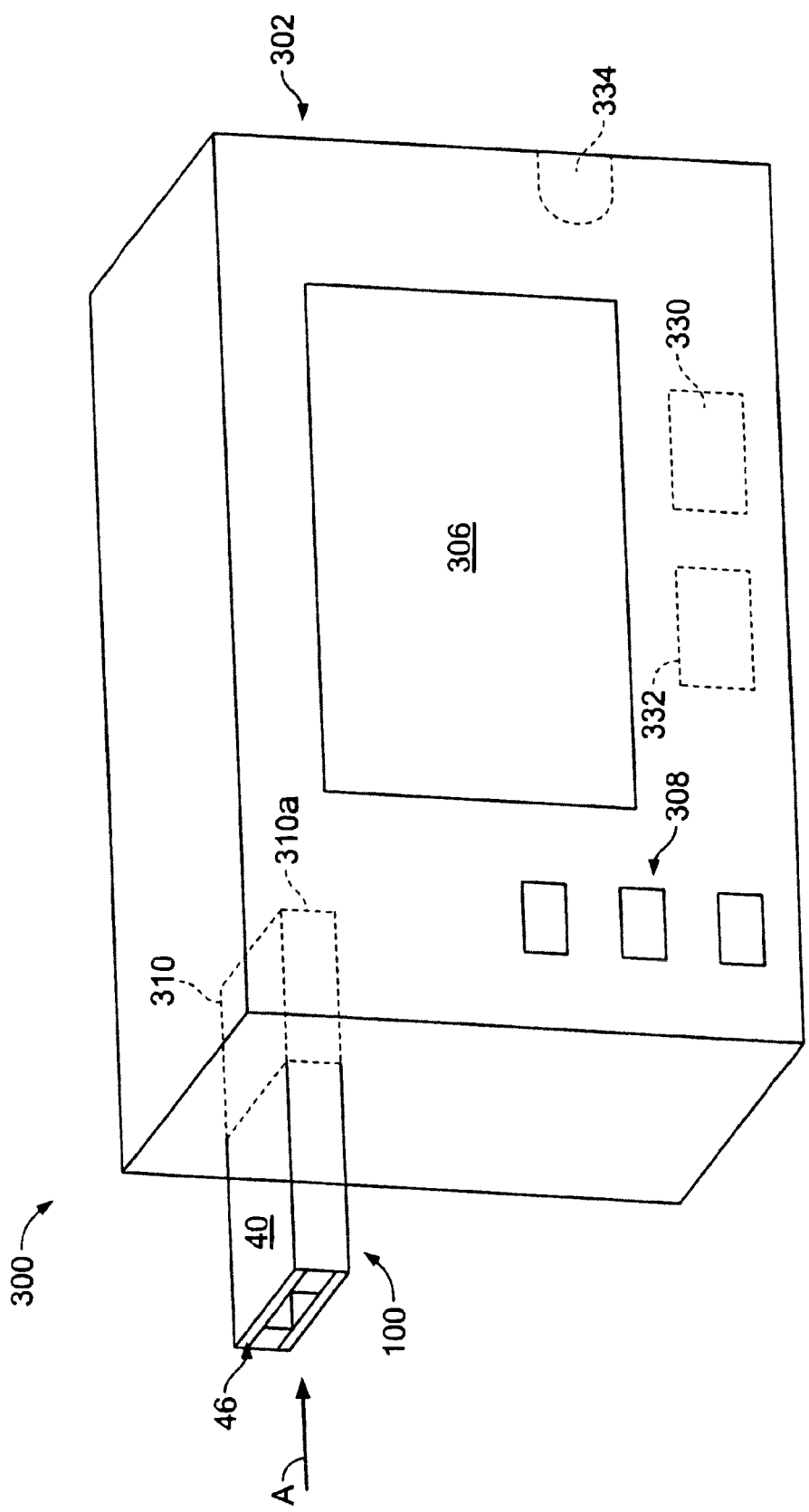
FIG. 8C is the meter or instrument of FIG. 8A with a test sensor being inserted therein according to one embodiment.

As shown in FIGS. 8B, 8C, the meter contacts 320 extend from the side surface 316 and are generally perpendicular to the insertion direction of the test sensor (see FIG. 8C with test sensor 100 being inserted in the direction of arrow A of FIG. 8C) into the meter or instrument 300. It is contemplated that the meter contacts may be installed on the side surface in such a manner that they are at an angle less than or greater than generally perpendicular to the insertion direction of the test sensor.

Referring to FIG. 8C, the test sensor 100 is loaded in the meter or instrument 300 along arrow A. Specifically, the second base end 46 (see FIG. 1a) is inserted initially into the test-sensor opening 310. The process of loading the test sensor shown in FIG. 8C is referred to as front-loading. During one insertion process, the meter contacts 320 slide over the upper base surface 40 of the test sensor 100. In one insertion process, the second base end 46 is moved into the test-sensor-opening 310 until contacting a back end 310a of the area that forms the test-sensor opening 310. This is referred to as a fully inserted position. The meter contacts make electrical contact with the test-sensor contacts when the test sensor is fully inserted in this process.

The memory device 330 is adapted to store analyte concentration readings, hematocrit readings, etc. The processor 332 processes information and communicates with the memory device 330. The instrument 300 also further includes a data port 334 that is adapted to communicate with a remote device (e.g., a computer) via a communications link. The communications link may be a wired system or wireless.

Some commercially available instruments or meters, such as those that are manufactured and/or sold by Bayer Healthcare LLC of Tarrytown, N.Y., may be designed to incorporate the features of the present invention, such as the Ascensia® CONTOUR® Blood Glucose Monitoring System, the Ascensia® BREEZE® and BREEZE®2 Blood Glucose Monitoring System, and the Ascensia® Elite® and Elite® XL Blood Glucose Monitoring System. It is contemplated that other instruments or meters, in addition to the ones listed above, may be designed to incorporate the features of the present invention. It is contemplated that the meter or instrument may be of a different shape or size than depicted in FIGS. 8A-8C.

Embodiment A

An electrochemical test sensor adapted to assist in determining the concentration of an analyte in a fluid sample, the test sensor comprising:
 a lid; and
 a base having a length and a width, the length of the base being greater than the width of the base, the base including at least a working electrode, a counter electrode and at least three test-sensor contacts for electrically connecting to a meter, the at least three test-sensor contacts being staggered along the width of the base from each other and being spaced along the length of the base from each other, the base and the lid assisting in forming a fluid chamber for receiving the fluid sample, and
 wherein the electrochemical test sensor further includes a reagent to assist in determining the concentration of the analyte in the fluid sample.

Embodiment B

The test sensor of embodiment A further including a spacer such that at least a portion of the spacer is located between the lid and the base, the lid, the base and the spacer assisting in forming the fluid chamber for receiving the fluid sample.

Embodiment C

The test sensor of embodiment A wherein the length of the base is at least 3 times greater than the width of the base.

Embodiment D

The test sensor of embodiment C wherein the length of the base is at least 4 times greater than the width of the base.

Embodiment E

The test sensor of embodiment A wherein the test-sensor contacts are in a generally polygonal shape.

Embodiment F

The test sensor of embodiment A wherein the electrochemical test sensor further includes at least four test-sensor contacts, the at least four test-sensor contacts being staggered along the width of the base from each other and being spaced along the length of the base from each other.

Embodiment G

The test sensor of embodiment A wherein the electrochemical test sensor further includes at least a third electrode.

Embodiment H

The test sensor of embodiment A wherein the reagent includes an enzyme, the enzyme being glucose oxidase or glucose dehydrogenase.

Embodiment I

An electrochemical test sensor adapted to assist in determining the concentration of an analyte in a fluid sample, the test sensor comprising:
 a lid; and
 a base having a length and a width, the length of the base being greater than the width of the base, the base including at least a working electrode, a counter electrode and at least three test-sensor contacts for electrically connecting to a meter, the at least three test-sensor contacts being spaced along the length of the base from each other, the base and the lid assisting in forming a fluid chamber for receiving the fluid sample, and
 wherein the electrochemical test sensor further includes a reagent to assist in determining the concentration of the analyte in the fluid sample.

Embodiment J

The test sensor of embodiment I further including a spacer such that at least a portion of the spacer is located between the lid and the base, the lid, the base and the spacer assisting in forming the fluid chamber for receiving the fluid sample.

Embodiment K

The test sensor of embodiment I wherein the length of the base is at least 3 times greater than the width of the base.

Embodiment L

The test sensor of embodiment K wherein the length of the base is at least 4 times greater than the width of the base.

Embodiment M

The test sensor of embodiment I wherein the test-sensor contacts are in a generally polygonal shape.

Embodiment N

The test sensor of embodiment I wherein the electrochemical test sensor further includes at least four test-sensor contacts, the at least four test-sensor contacts being spaced along the length of the base from each other.

Embodiment O

The test sensor of embodiment I wherein the electrochemical test sensor further includes at least a third electrode.

Embodiment P

The test sensor of embodiment I wherein the reagent includes an enzyme, the enzyme being glucose oxidase or glucose dehydrogenase.

Process Q

A method of determining an analyte concentration of a fluid sample, the method comprising the acts of:
 providing an electrochemical test sensor, the test sensor including a lid, a base and a reagent that assists in determining the concentration of the analyte in the fluid sample, the base having a length and a width, the length of the base being greater than the width of the base, the base including at least a working electrode, a counter electrode and at least three test-sensor contacts, the at least three test-sensor contacts being spaced along the length of the base from each other, the base and the lid assisting in forming a fluid chamber for receiving the fluid sample;
 providing a meter including a test-sensor opening, the test-sensor opening being formed between a bottom surface, a top surface and corresponding side surfaces, the side surfaces bridging the bottom and top surfaces, at least one of the side surfaces including a plurality of side-mounted meter contacts;
 placing the test sensor into the test-sensor opening such that the plurality of side-mounted meter contacts electrically contact a respective one of the test-sensor contacts of the electrochemical test sensor; and
 determining the analyte concentration using electrical signals from the side-mounted meter contacts.

Process R

The method of process Q further including a spacer such that at least a portion of the spacer is located between the lid and the base, the lid, the base and the spacer assisting in forming the fluid chamber for receiving the fluid sample.

Process S

The method of process Q wherein the length of the base is at least 3 times greater than the width of the base.

Process T

The method of process S wherein the length of the base is at least 4 times greater than the width of the base.

Process U

The method of process Q wherein the test-sensor contacts are in a generally polygonal shape.

Process V

The method of process Q wherein the electrochemical test sensor further includes at least four test-sensor contacts, the at least four test-sensor contacts being spaced along the length of the base from each other.

Process W

The method of process Q wherein the fluid sample is blood.

Process X

The method of process Q wherein the analyte is glucose.

Process Y

The method of process Q wherein the plurality of side-mounted meter contacts is generally perpendicular to the direction of the electrochemical test sensor being placed into the test-sensor opening.

Process Z

The method of process Q wherein the at least three test-sensor contacts are staggered along the width of the base with each other.

Process AA

The method of process Q wherein the placing of the test sensor into the test-sensor opening is performed by front-loading.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the attached claims.

The invention claimed is:

1. An electrochemical test sensor adapted to assist in determining the concentration of an analyte in a fluid sample, the test sensor comprising:
a lid; and
a base having a length and a width, the length being perpendicular to the width, the length of the base being greater than the width of the base, the base including at least a working electrode, a counter electrode and at least three test-sensor contacts for electrically connecting to a meter, the test sensor contacts being electrically connected to either the working electrode or the counter electrode, each end of the at least three test-sensor contacts being staggered along the width and the length of the base from each other, the at least three test-sensor contacts being spaced from and not overlapping along the length of the base with each other, the base and the lid assisting in forming a fluid chamber for receiving the fluid sample, and
a reagent to assist in determining the concentration of the analyte in the fluid sample.

2. The test sensor of claim 1 further including a spacer such that at least a portion of the spacer is located between the lid and the base, the lid, the base and the spacer assisting in forming the fluid chamber for receiving the fluid sample.

3. The test sensor of claim 1 wherein the length of the base is at least 3 times greater than the width of the base.

4. The test sensor of claim 3 wherein the length of the base is at least 4 times greater than the width of the base.

5. The test sensor of claim 1 wherein the test-sensor contacts are in a polygonal shape.

6. The test sensor of claim 1 wherein the electrochemical test sensor further includes at least four test-sensor contacts, each end of the at least four test-sensor contacts being staggered along the width and the length of the base from each other, the at least four test-sensor contacts being spaced from and not overlapping along the length of the base with each other.

7. The test sensor of claim 1 wherein the electrochemical test sensor further includes at least a third electrode.

8. The test sensor of claim 1 wherein the reagent includes an enzyme, the enzyme being glucose oxidase or glucose dehydrogenase.

9. An electrochemical test sensor adapted to assist in determining the concentration of an analyte in a fluid sample, the test sensor comprising:
a lid; and
a base having a length and a width, the base further including a first end and a second, opposing end being separated by the length, the length being perpendicular to the width, the length of the base being greater than the width of the base, the base including at least a working electrode, a counter electrode and at least three test-sensor contacts for electrically connecting to a meter, the test sensor contacts being electrically connected to either the working electrode or the counter electrode, each end of the at least three test-sensor contacts being staggered along the width and the length of the base from each other, the at least three test-sensor contacts being spaced from and not overlapping along the length of the base with each other, the base and the lid assisting in forming a fluid chamber for receiving the fluid sample, the fluid chamber being located at the first end and at least one of the test-sensors contacts being located at the second, opposing end from the fluid chamber; and
a reagent to assist in determining the concentration of the analyte in the fluid sample.

10. The test sensor of claim 9 further including a spacer such that at least a portion of the spacer is located between the lid and the base, the lid, the base and the spacer assisting in forming the fluid chamber for receiving the fluid sample.

11. The test sensor of claim 9 wherein the length of the base is at least 3 times greater than the width of the base.

12. The test sensor of claim 11 wherein the length of the base is at least 4 times greater than the width of the base.

13. The test sensor of claim 9 wherein the test-sensor contacts are in a polygonal shape.

14. The test sensor of claim 9 wherein the electrochemical test sensor further includes at least four test-sensor contacts, each end of the at least four test-sensor contacts being staggered along the width and the length of the base from each other, the at least four test-sensor contacts being spaced from and not overlapping along the length of the base with each other.

15. The test sensor of claim 9 wherein the electrochemical test sensor further includes at least a third electrode.

16. The test sensor of claim 9 wherein the reagent includes an enzyme, the enzyme being glucose oxidase or glucose dehydrogenase.

* * * * *